United States Patent
Nagase et al.

(10) Patent No.: US 10,525,015 B2
(45) Date of Patent: Jan. 7, 2020

(54) NALFURAFINE-CONTAINING PERCUTANEOUS ABSORPTION PATCH

(71) Applicant: UNIVERSITY OF TSUKUBA, Tsukuba-shi, Ibaraki (JP)

(72) Inventors: Hiroshi Nagase, Tsukuba (JP); Makiko Tada, Tokyo (JP); Megumi Yashima, Tokyo (JP); Takeshi Saiki, Tokyo (JP)

(73) Assignee: UNIVERSITY OF TSUKUBA, Tsukuba (JP)

( * ) Notice: Subject to any disclaimer, the term of this patent is extended or adjusted under 35 U.S.C. 154(b) by 38 days.

(21) Appl. No.: 15/739,156

(22) PCT Filed: Jun. 24, 2016

(86) PCT No.: PCT/JP2016/068860
§ 371 (c)(1),
(2) Date: Feb. 6, 2018

(87) PCT Pub. No.: WO2016/208729
PCT Pub. Date: Dec. 29, 2016

(65) Prior Publication Data
US 2018/0369161 A1 Dec. 27, 2018

(30) Foreign Application Priority Data
Jun. 24, 2015 (JP) .................... 2015-126282

(51) Int. Cl.
| | | |
|---|---|---|
| *A61K 9/70* | (2006.01) | |
| *A61K 47/32* | (2006.01) | |
| *A61K 31/485* | (2006.01) | |
| *A61K 9/00* | (2006.01) | |
| *A61K 47/06* | (2006.01) | |
| *A61P 17/04* | (2006.01) | |

(52) U.S. Cl.
CPC .......... *A61K 9/7084* (2013.01); *A61K 9/0014* (2013.01); *A61K 31/485* (2013.01); *A61K 47/06* (2013.01); *A61K 47/32* (2013.01); *A61P 17/04* (2018.01)

(58) Field of Classification Search
None
See application file for complete search history.

(56) References Cited

FOREIGN PATENT DOCUMENTS

| | | | |
|---|---|---|---|
| JP | S62-298524 A | 12/1987 | |
| JP | 2013-147459 A | 8/2013 | |
| JP | 2013147459 | * 8/2013 | |
| WO | WO-2009026135 A2 | * 2/2009 | ........... A61K 9/7084 |

OTHER PUBLICATIONS

Owada et al., "Uremic pruritus," *Japanese Journal of Clinical Medicine*, 50 (Special Extra Issue): 867-872 (1992).
Tsai et al., "Effect of Barrier Disruption by Acetone Treatment on the Permeability of Compounds with Various Lipophilicities: Implications for the Permeability of Compromised Skin," *J. Pharm. Sci.*, 90(9): 1242-1254 (2001).
Japanese Patent Office, International Search Report in International Patent Application No. PCT/JP2016/068860 (dated Aug. 16, 2016).

* cited by examiner

*Primary Examiner* — Robert A Wax
*Assistant Examiner* — Melissa S Mercier
(74) *Attorney, Agent, or Firm* — Leydig, Voit & Mayer, Ltd.

(57) ABSTRACT

The present invention relates to a nalfurafine-containing percutaneous absorption patch having a support, a drug layer and a control layer which are laminated successively, wherein the drug layer contains at least one kind of a drug selected from the group consisting of nalfurafine and a salt thereof, and capable of maintaining a given level of drug skin permeation amount without permeation of an excess amount of the drug through the skin in a short time even when applied to the skin in which the horny cell layer and the like are damaged and the skin barrier is insufficient.

9 Claims, No Drawings

NALFURAFINE-CONTAINING PERCUTANEOUS ABSORPTION PATCH

TECHNICAL FIELD

The present invention relates to a percutaneous absorption patch containing nalfurafine.

BACKGROUND ART

Pruritus (itching) is a sensation peculiar to the skin, mucous membrane and cornea and a symptom that we feel in our daily life. It is a symptom that is most frequently felt painful in skin diseases accompanying inflammation. Diseases associated with itching include visceral diseases such as renal disease (chronic renal failure), hepatic disease, diabetes, malignant tumor and the like in addition to those caused by skin diseases such as urticaria, atopic dermatitis and the like. Different from peripheral itching caused by skin diseases, itching caused by visceral diseases is a central itching involving the opioid system (endogenous opioid and opioid receptor) and is clinically refractory. When this central itching becomes severe, the scratching behavior and annoyed feeling increase to a level preventing staying still, which in turn disturbs everyday life and causes sleep disorder, etc., thereby markedly lowering the QOL (Quality of Life) of patients. As a therapeutic drug for such central itching, nalfurafine is attracting attention in recent years.

Nalfurafine is an opioid K (kappa) receptor agonist, a drug that inherently shows an antipruritic effect on central itching involving the opioid system. At present, as a nalfurafine-containing pharmaceutical product, an oral preparation Remitch capsule 2.5 μg (Torii Pharmaceutical Co., Ltd.) is on the market.

Oral administration is the most common method of administering drugs and is generally regarded as the first choice since it is superior in terms of QOL of patients. However, it may cause a transient increase in the blood drug concentration and expression of strong side effects. In addition, since drug supply is not sustainable, the effective blood concentration cannot be maintained for a long time and sustainability of the effect sometimes becomes insufficient.

Indeed, nalfurafine oral preparations show a dose-dependent increase in the expression rate of side effects such as insomnia, constipation, drowsiness and the like, which suggests a possibility that a transient increase in the blood nalfurafine concentration causes expression of side effects. Also, a decrease in the blood nalfurafine concentration and attenuation of antipruritic effect were observed within 24 hours after a single administration.

Therefore, the development of a nalfurafine-containing preparation that suppresses a transient increase in the blood drug concentration causing side effects, and can maintain the blood drug concentration constant for a long time has been desired.

As a preparation that can suppress a transient increase in the blood drug concentration and maintain blood drug concentration constant for a long time, a percutaneous absorption patch is available. Percutaneous absorption patches were generally developed on the premise that they are applied to normal skin without trauma, dermatitis and the like. This aims to suppress permeation of a drug through the skin by the skin barrier function of the horny cell layer and the like, thereby preventing easy occurrence of a transient increase in the blood drug concentration (patent document 1).

However, in patients with severe pruritus to which nalfurafine is applied, they often scratch the whole body and damage the horny cell layer and the like, thus sometimes producing a wide area where skin barrier function is insufficient. When a percutaneous absorption patch containing nalfurafine is applied to such patients, the skin barrier function is not sufficiently exhibited and an excess amount of nalfurafine permeates through the skin in a short time. As a result, there is a risk of causing a transient increase in the blood nalfurafine concentration. Generally, the risk of causing a transient increase in the blood drug concentration can be avoided by lowering the drug concentration of the percutaneous absorption patch. In this case, it is possible that the decrease in the drug concentration of the patch causes failure to maintain a given drug skin permeation amount and makes it difficult to supply the drug into the blood for a long time. At the present stage, no technology has been developed that solves these two problems at the same time.

Thus, the development a nalfurafine-containing percutaneous absorption patch capable of maintaining a given level of drug skin permeation amount without permeation of an excess amount of the drug through the skin in a short time even when applied to the skin in which the horny cell layer and the like are damaged and the skin barrier function is insufficient has been demanded.

DOCUMENT LIST

Patent Documents patent document 1: JP-A-2013-147459

SUMMARY OF THE INVENTION

Problems to be Solved by the Invention

The present invention has been made in view of the aforementioned situation and aims to provide a nalfurafine-containing percutaneous absorption patch capable of maintaining a given level of drug skin permeation amount without permeation of an excess amount of the drug through the skin in a short time even when applied to the skin in which the horny cell layer etc. are damaged and the skin barrier function is insufficient.

Means of Solving the Problems

The present inventors have conducted intensive studies in an attempt to solve the aforementioned problems and found that a percutaneous absorption patch comprising a support, a drug layer and a control layer, which are successively laminated, and at least one kind of a drug selected from the group consisting of nalfurafine and a salt thereof is contained in the drug layer is capable of maintaining a given level of drug skin permeation amount without permeation of an excess amount of the drug through the skin in a short time even when applied to the skin in which the horny cell layer and the like are damaged and the skin barrier is insufficient. Based on this finding, they have completed the present invention.

That is, the present invention relates to the following (1)-(10).

(1) A percutaneous absorption patch comprising a support, a drug layer and a control layer which are laminated successively, wherein the aforementioned drug layer comprises 0.0001-10 mass % of at least one kind of a drug selected from the group consisting of nalfurafine and a salt thereof.

(2) A percutaneous absorption patch comprising a support, a drug layer and a control layer which are laminated successively, wherein the aforementioned drug layer comprises 0.0001-10 mass % of at least one kind of a drug selected from the group consisting of nalfurafine and a salt thereof, and a styrene block copolymer as a base.

(3) A percutaneous absorption patch comprising a support, a drug layer and a control layer which are laminated successively, wherein the aforementioned drug layer comprises 0.0001-10 mass % of at least one kind of a drug selected from the group consisting of nalfurafine and a salt thereof, and a styrene block copolymer as a base, and the aforementioned control layer comprises a chain hydrocarbon polymer.

(4) The percutaneous absorption patch of (3) wherein the styrene block copolymer is a styrene-isoprene-styrene block copolymer.

(5) The percutaneous absorption patch of (3) wherein the aforementioned control layer further comprises 10-90 mass % of at least one kind selected from the group consisting of a plasticizer and a tackifier.

(6) The percutaneous absorption patch of (3) wherein the aforementioned control layer comprises polyisobutylene as a chain hydrocarbon polymer, and 10-90 mass % of at least one kind selected from the group consisting of a plasticizer and a tackifier.

(7) The percutaneous absorption patch of (5) or (6) wherein the aforementioned plasticizer is liquid paraffin.

(8) The percutaneous absorption patch of (5) or (6) wherein the aforementioned tackifier is at least one kind selected from the group consisting of rosin ester, a terpene-based resin and an alicyclic hydrocarbon resin.

(9) The percutaneous absorption patch of any of (4)-(6) wherein, in a rat skin permeation test, the maximum value of a drug skin permeation amount per unit time is not more than 1000 $ng/cm^2/hr$.

(10) The percutaneous absorption patch of any of (4)-(6) wherein, in a rat skin permeation test, a ratio of the drug skin permeation amount per unit time 10 hr later to the maximum value of the drug skin permeation amount per unit time (drug skin permeation amount per unit time 10 hr later/maximum value of drug skin permeation amount per unit time) is not less than 0.5.

Effect of the Invention

The present invention can provide a nalfurafine-containing percutaneous absorption patch capable of maintaining a given level of drug skin permeation amount without permeation of an excess amount of the drug through the skin in a short time even when applied to the skin in which the horny cell layer and the like are damaged and the skin barrier function is insufficient.

DESCRIPTION OF EMBODIMENTS

The nalfurafine-containing percutaneous absorption patch of the present invention (hereinafter to be also referred to as "the percutaneous absorption patch of the present invention" in the present specification) is explained in detail in the following. Exemplifications described in the present specification do not particularly limit the present invention.

In the present specification, "without permeation of an excess amount of the drug through the skin in a short time" means that an excess amount of a drug does not permeate the skin in a rat skin permeation test. That is, when the drug skin permeation amount per unit time is not more than 1000 $ng/cm^2/hr$, "without permeation of an excess amount of the drug through the skin in a short time" is used, and when it exceeds 1000 $ng/cm^2/hr$, "with permeation of an excess amount of the drug through the skin in a short time" is used.

In the present specification, "capable of maintaining a given level of drug skin permeation amount" means that, even after lapse of not less than 8 hr from the application of the patch to the skin, a difference between a drug skin permeation amount per unit time and the maximum value of the drug skin permeation amount per unit time up to that time is small in a rat skin permeation test. In the percutaneous absorption patch of the present invention, when a ratio of the drug skin permeation amount per unit time 10 hr later from the application of the patch to the skin to the maximum value of the drug skin permeation amount per unit time (drug skin permeation amount per unit time 10 hr later from the application of the patch to the skin/maximum value of drug skin permeation amount per unit time) is not less than 0.5, "capable of maintaining a given level of drug skin permeation amount" is used, and when it is less than 0.5, "incapable of maintaining a given level of drug skin permeation amount" is used.

In the present specification, the "drug skin permeation amount per unit time" is a value obtained by dividing a difference between a cumulative drug skin permeation amount per unit area at each sampling time and a cumulative drug skin permeation amount per unit area at the previous sampling time in a rat skin permeation test by a sampling interval (hr).

The percutaneous absorption patch of the present invention comprises a support, a drug layer and a control layer, which are laminated successively. In the percutaneous absorption patch of the present invention, moreover, a separating material that covers an adhesive part to the skin and is peeled off when in use may be provided to protect the adhesive part to the skin until use.

In the percutaneous absorption patch of the present invention, moreover, a skin adhesive layer to afford good adhesiveness to the skin and good release property may be laminated on the further skin side of the control layer as long as the object of the present invention can be achieved.

As a support to be used for the percutaneous absorption patch of the present invention, one free from an influence on the release and stability of a drug is desirable and is not particularly limited as long as it can be adhered or anchored. A support having flexibility to a level that prevents occurrence of a remarkable foreign body sensation when the percutaneous absorption patch is adhered to the skin surface is preferable, and any elastic or non-elastic one can be used.

For example, one kind selected from the group consisting of sheet, porous body, foam, cloth, non-woven fabric and the like, which are produced by forming a material such as synthetic resin (mainly containing polyethylene, polypropylene, polyester, polyvinyl acetate, ethylene vinyl acetate copolymer, polyvinyl chloride, nylon, polyurethane and the like), paper and metal and the like, or a laminate obtained by laminating two or more kinds selected from the aforementioned group, can be used.

A drug contained in the percutaneous absorption patch of the present invention is selected from the group consisting of nalfurafine and a salt thereof, and both a free form and a salt can be used. Particularly, nalfurafine in a free form is preferable.

When a salt of nalfurafine is used, it is generally a salt of an acid capable of forming a salt with nalfurafine, and is not particularly limited as long as it is a medically or pharmaceutically acceptable salt. For example, inorganic acid salts such as nalfurafine hydrochloride, nalfurafine sulfate, nalfurafine phosphate, nalfurafine nitrate, nalfurafine borate, nalfurafine sulfonate and nalfurafine carbonate and the like, organic acid salts such as nalfurafine lactate, nalfurafine formate, nalfurafine acetate, nalfurafine tartrate, nalfurafine malate and nalfurafine citrate and the like, and the like can be mentioned, and nalfurafine hydrochloride is preferable.

It is also possible to blend a salt of nalfurafine in a patch together with an additive having basicity, and convert the salt to a free form. Examples of such additive having basicity include diisopropanolamine, triisopropanolamine, monoethanolamine, diethanolamine, triethanolamine, sodium phosphate, sodium hydroxide, potassium hydroxide and calcium hydroxide and the like. One kind may be used singly, or two or more kinds may be used in combination.

While the amount of the drug to be contained in the percutaneous absorption patch of the present invention is not particularly limited as long as a percutaneous absorption patch can be formulated, sufficient efficacy cannot be obtained at less than 0.0001 mass % relative to the total amount drug layer and the risk of expressing the side effects becomes high when it exceeds 10 mass %. Therefore, 0.0001-10 mass % is preferable, 0.001-5 mass % is more preferable, and 0.01-1 mass % is further preferable.

In the percutaneous absorption patch of the present invention, the drug can be contained in a dissolution state, supersaturated crystal state or dispersion state.

The drug layer of the percutaneous absorption patch of the present invention can contain other central antipruritic drug, anti-histamine drug, antiinflammatory agent and the like in combination as long as the effect of the present invention is not impaired by an influence on the stability and efficacy of nalfurafine and the like.

Examples of other central antipruritic drug include opioid K receptor agonists (e.g., pentazocine and the like) other than nalfurafine, opioid μ receptor antagonists such as naloxone, nalmefene, naltrexone and the like, serotonin 5-$HT_3$ receptor antagonists such as Ondanserotron and the like, and the like.

Examples of the anti-histamine drug include diphenhydramine, diphenhydramine hydrochloride, chlorpheniramine maleate and the like.

Examples of the antiinflammatory agent include adrenal cortical steroids such as dexamethasone propionate, betamethasone valerate, fluocinolone acetonide and the like; non-steroidal antiinflammatory agents such as ibuprofen piconol, suprofen, bufexamac and the like, and the like.

One or more kinds can be selected from these other drugs and used together with nalfurafine, and can be contained in an amount generally used for a percutaneous absorption patch.

The drug layer of the percutaneous absorption patch of the present invention contains a styrene block copolymer as a base. While the styrene block copolymer is not particularly limited as long as it can maintain a drug, for example, styrene-isoprene block copolymer, styrene-isoprene-styrene block copolymer, styrene-butadiene block copolymer, styrene-butadiene-styrene block copolymer, styrene-ethylene-butylene-styrene block copolymer and the like can be mentioned. One kind may be used singly, or two or more kinds may be used in combination. A styrene-isoprene-styrene block copolymer is preferably used in the present invention.

In the percutaneous absorption patch of the present invention, examples of the styrene-isoprene-styrene block copolymer to be contained in the drug layer include JSRSIS5002, JSRSIS5229, JSRSIS5250P, JSRSIS5403 and JSRSIS5505P (all manufactured by JSR Corporation), Kraton D-KX401CS, Kraton D-1107CU, Kraton D-1161JP and Kraton D-KX406CP (all manufactured by Kraton polymer Japan KK), Quintac 3421, Quintac 3620 and Quintac 3520 (all manufactured by Zeon Corporation) and the like. One kind may be used singly, or two or more kinds may be used in combination.

In the percutaneous absorption patch of the present invention, the drug layer can appropriately contain, besides those mentioned above, various components acceptable for producing pharmaceutical products, namely, plasticizer, tackifier, drug dissolving agent, absorption promoter, pH adjuster, antioxidant, filler, crosslinking agent, preservative, ultraviolet absorber and the like, as long as the effect of the present invention is not impaired. The kinds and amounts thereof are not particularly limited as long as they can be formulated as a percutaneous absorption patch.

Examples of the plasticizer include petroleum oil (liquid paraffin, paraffin process oil, naphthene process oil, aromatic process oil and the like), squalane, squalene, vegetable oil (olive oil, camellia oil, castor oil, tall oil, peanut oil and the like), silicone oil, liquid rubber (liquid polybutene, liquid isoprene rubber and the like), liquid fatty acid esters (isopropyl myristate, hexyl laurate, diethyl sebacate, diisopropyl sebacate and the like), polyhydric alcohol (diethylene glycol, polyethylene glycol, propylene glycol, dipropylene glycol, glycerol and the like), triacetine, triethyl citrate, glycol salicylate and crotamiton and the like. One kind may be used singly, or two or more kinds may be used in combination.

Examples of the tackifier include petroleum resin (aliphatic hydrocarbon resin, alicyclic hydrocarbon resin, aromatic hydrocarbon resin and the like), rosin resin (rosin, rosin ester and the like), terpene based resin, phenol resin, xylene resin and coumarone indene resin and the like, medically or pharmaceutically acceptable tackifier resin. One kind may be used singly, or two or more kinds may be used in combination.

While the drug dissolving agent is not particularly limited as long as it shows a drug dissolving action and does not exert a remarkable influence on the stability of the drug, N-methyl-2-pyrrolidone, isopropyl myristate, isopropyl palmitate, diisopropyl adipate, sorbitan monooleate, propylene glycol caprylate, propylene carbonate, oleyl alcohol, lauryl alcohol, benzyl alcohol, triacetine, crotamiton and 1-menthol and the like can be mentioned. One kind may be used singly, or two or more kinds may be used in combination.

The absorption promoter may be any of the compounds conventionally acknowledged to show a percutaneous absorption promoting action on the skin. Examples thereof include organic acid (lactic acid, propionic acid, cinnamic acid, nicotinic acid, phthalic acid, oxalic acid, fumaric acid, maleic acid, succinic acid, tartaric acid, citric acid, salicylic acid and the like), organic acid ester (myristyl lactate, cetyl lactate, lauryl lactate, methyl cinnamate, methyl salicylate, ethylene glycol salicylate, ethyl acetate, propyl acetate, benzyl acetate and the like), fatty acid having a carbon number of 6-32 (caproic acid, enanthic acid, caprylic acid, pelargric acid, capric acid, undecylic acid, lauric acid, tridecylic acid, myristic acid, pentadecylic acid, palmitic acid, heptadecanoic acid, stearic acid, isostearic acid, oleic acid, nonadecanoic acid, arachidonic acid, linoleic acid, linolenic acid, behenic acid, lignoceric acid, cerotic acid, heptacosanic acid, montanic acid, melissic acid, elaidic acid, brassidic acid and the like), fatty acid ester and polybasic acid ester (isopropyl myristate, diisopropyl adipate, myristyl palmitate, isopropyl palmitate, oleyl oleate, diethyl sebacate, diisopropyl sebacate, stearyl stearate, ethylhexyl stearate, myristyl myristate and the like), glycerol fatty acid esters (glyceryl myristate, self-emulsifying type glyceryl monostearate, glyceryl monocaprylate, glyceryl tri(caprylate/caprate) and the like), propylene glycol ester of fatty acid (propylene glycol dicaprate, propylene glycol caprylate, propylene glycol dicaprylate, self-emulsifying type propylene glycol stearate, propylene glycol monostearate and the like), sorbitan fatty acid ester (sorbitan monopalmitate, sorbitan monostearate, sorbitan trioleate and the like), sucrose fatty acid ester, aliphatic alcohol (heptyl alcohol, octyl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, oleyl alcohol, nonadecyl alcohol, eicosyl alcohol, ceryl alcohol, melissyl alcohol, cetostearyl alcohol and the like), aromatic alcohol (benzyl alcohol and the like), polyhydric alcohol (ethylene glycol, glycerol, polyethylene glycol, propylene glycol, polypropylene glycol, hexanetriol, butylene glycol and the like), animal and vegetable oils (peppermint oil, turpentine oil, eucalyptus oil, orange oil, almond oil, olive oil, camellia oil, persic oil, soybean oil, sesame oil, corn oil, coconut oil, castor oil, safflower oil, sunflower oil, soybean lecithin and the like), terpene based compound (terpineol, cineol, menthol, isomenthol, menthone, piperitone, pulegone, ionone, carvone, limonene, camphor, borneol, geraniol, thymol, nerol and the like), phenylpropanoid compound (eugenol and the like), pyrrolidone (2-pyrrolidone, 1-methyl-2-pyrrolidone, 5-methyl-2-pyrrolidone, 1,5-dimethylpyrrolidone, 1-ethylpyrrolidone, pyrrothiodecane and the like), urea (urea, thiourea and the like), hydrocarbons (squalane, squalene and the like), azacycloalkane (1-dodecylazacycloheptan-2-one (Azone) and a derivative thereof and the like), polysorbate (polysorbate 20, polysorbate 40, polysorbate 60, polysorbate 65, polysorbate 80 and the like), polyoxyethylene hydrogenated castor oil (polyoxyethylene hydrogenated castor oil, polyoxyethylene hydrogenated castor oil 5, polyoxyethylene hydrogenated castor oil 10, polyoxyethylene hydrogenated castor oil 20, polyoxyethylene hydrogenated castor oil 40, polyoxyethylene hydrogenated castor oil 50, polyoxyethylene hydrogenated castor oil 60, polyoxyethylene hydrogenated castor oil 100 and the like), polyoxyethylene alkyl ethers (polyoxyethylene lauryl ether, polyoxyethylene cetyl ether, polyoxyethylene stearyl ether, polyoxyethylene oleyl ether, polyoxyethylene behenyl ether and the like), triacetine, crotamiton, propylene carbonate and the like. One kind may be used singly, or two or more kinds may be used in combination.

Examples of the pH adjuster include acetic acid, formic acid, lactic acid, tartaric acid, oxalic acid, glycolic acid, malic acid, citric acid, succinic acid, fumaric acid, phosphoric acid, hydrochloric acid, nitric acid, sulfuric acid and salts of these, sodium hydroxide, potassium hydroxide, calcium hydroxide, arginine, methylamine, ethylamine, propylamine, dimethylamine, diethylamine, dipropylamine, trimethylamine, triethylamine, tripropylamine, monomethanolamine, monoethanolamine, monopropanolamine, dimethanolamine, diethanolamine, dipropanolamine, trimethanolamine, triethanolamine, isopropanolamine, diisopropanolamine, triisopropanolamine, aqueous ammonia, guanidine carbonate, sodium hydrogen carbonate, ammonium carbonate and the like. One kind may be used singly, or two or more kinds may be used in combination.

Examples of the antioxidant include tocopherol and these ester derivative, ascorbic acid, sodium thiosulfate, propyl gallate, ascorbyl stearate, nordihydroguaiuretic acid, sodium edetate, sodium bisulfite, dibutylhydroxytoluene, butylhydroxyanisole and the like. One kind may be used singly, or two or more kinds may be used in combination.

Examples of the filler include calcium carbonate, magnesium carbonate, silicic acid, silicate (aluminum silicate, magnesium silicate and the like), bentonite, kaolin, talc, barium sulfate, calcium sulfate, calcium zincate, zinc oxide and titanium oxide and the like. One kind may be used singly, or two or more kinds may be used in combination.

Examples of the crosslinking agent include thermosetting resin (amino resin, phenol resin, epoxy resin, alkyd resin, unsaturated polyester and the like), organic crosslinking agent (organic peroxide and the like), inorganic crosslinking agent (metal, metal compound and the like), isocyanate compound and block isocyanate compound and the like. One kind may be used singly, or two or more kinds may be used in combination.

Examples of the preservative include thymol, isopropylmethylphenol, benzoic acid and a salt thereof, sorbic acid and a salt thereof, methyl paraoxybenzoate, ethyl paraoxybenzoate, propyl paraoxybenzoate, butyl paraoxybenzoate, benzyl alcohol, benzalkonium chloride, benzethonium chloride and the like. One kind may be used singly, or two or more kinds may be used in combination.

Examples of the ultraviolet absorber include p-aminobenzoic acid derivative, anthranilic acid derivative, salicylic acid derivative, coumarin derivative, amino acid derivative, imidazoline derivative, benzophenone derivative, cinnamic acid derivative, pyrimidine derivative and dioxane derivative and the like. One kind may be used singly, or two or more kinds may be used in combination.

In the percutaneous absorption patch of the present invention, the control layer contains a chain hydrocarbon polymer as a base. A chain hydrocarbon polymer is preferably contained in 10-90 mass %, more preferably 20-80 mass %, relative to the total amount of the control layer.

In the percutaneous absorption patch of the present invention, the chain hydrocarbon polymer contained in the control layer may be linear chain or branched chain, or saturated or unsaturated as long as it is a polymer using hydrocarbon as a monomer, and the aforementioned hydrocarbon has a chain structure. For example, polyisobutylene, polyisoprene, hydrogenated polyisoprene, polybutadiene, hydrogenated polybutadiene, polybutene, polypropylene and polyethylene and the like can be mentioned. One kind may be used singly, or two or more kinds may be used in combination, and polyisobutylene is preferably used.

In the percutaneous absorption patch of the present invention, examples of the polyisobutylene contained in the control layer include Oppanol B-10SFN, Oppanol B-11SFN, Oppanol B-12SFN, Oppanol B-13SFN, Oppanol B-15SFN, Oppanol B-30SF, Oppanol B-50SF, Oppanol B-80, Oppanol B-100, Oppanol B-150 and Oppanol B-200 (all manufactured by BASF Japan Ltd.), Tetrax 3T, Tetrax 4T, Tetrax 5T, Tetrax 6T, Himol 4H, Himol 5H, Himol 5.5H and Himol 6H (all manufactured by JX Energy Co., Ltd.) and the like. One kind may be used singly, or two or more kinds may be used in combination.

The control layer in the percutaneous absorption patch of the present invention is desirably imparted with adhesiveness by adding a plasticizer and/or a tackifier. The adhesiveness to the skin can be freely changed by the content of the plasticizer and/or tackifier. To maintain an adhesive force permitting adhesion to the skin for a long time and avoid an adhesive residue on the skin on detachment, at least one kind selected from the group consisting of a plasticizer and a tackifier is preferably contained in 10-90 mass % relative to the total mass of the control layer. The aforementioned content is more preferably 20-80 mass %, further preferably 30-70 mass %.

The kind and content of the plasticizer to be used in the control layer of the percutaneous absorption patch of the present invention is not particularly limited as long as it can be formulated as a percutaneous absorption patch. Examples thereof include petroleum oil (liquid paraffin, paraffin process oil, naphthene process oil, aromatic process oil and the like), squalane, squalene, vegetable oil (olive oil, camellia oil, castor oil, tall oil, peanut oil and the like), silicone oil, liquid rubber (liquid polybutene, liquid isoprene rubber and the like), liquid fatty acid esters (isopropyl myristate, hexyl laurate, diethyl sebacate, diisopropyl sebacate and the like), polyhydric alcohol (diethylene glycol, polyethylene glycol, propylene glycol, dipropylene glycol and the like), triacetine, triethyl citrate, glycol salicylate and crotamiton and the like. One kind may be used singly, or two or more kinds may be used in combination. Preferably, polyhydric alcohol, liquid paraffin, liquid polybutene, diethyl sebacate and isopropyl myristate are used, and liquid paraffin and liquid polybutene are more preferably used.

Examples of the liquid paraffin include Moresco White P-40, Moresco White P-55, Moresco White P-60, Moresco White P-70, Moresco White P-80, Moresco White P-100, Moresco White P-120, Moresco White P-150, Moresco White P-200, Moresco White P-260, Moresco White P-350P, Moresco Violess U-6, Moresco Violess U-7 and Moresco Violess U-8 (all manufactured by MORESCO Corporation), Haikol K-140N, Haikol K-160, Haikol K-230, Haikol K-290, Haikol K-350, Haikol M-52, Haikol M-72, Haikol M-172 and Haikol M-352 (all manufactured by KANEDA Co., Ltd.), Cosmo White P60, Cosmo White P70, Cosmo White P120, Cosmo White P200, Cosmo White P260 and Cosmo White P350P (all manufactured by Cosmo Oil Co., Ltd.), JX High White 350 (manufactured by JX Energy Co., Ltd.), KAYDOL (manufactured by SONNEBORN LLC.) and the like. One kind may be used singly, or two or more kinds may be used in combination.

Examples of the liquid polybutene include LV-7, LV-50, LV-100, HV-15, HV-35, HV-50, HV-100, HV-300, HV-1900 and SV-7000 (all manufactured by JX Energy Co., Ltd.), Nissan Polybutene (manufactured by NOF CORPORATION), PB680, PB950, PB1300, PB1400, PB2000 and PB2400 (all manufactured by Daelim) and the like. One kind may be used singly, or two or more kinds may be used in combination.

The kind and content of the tackifier to be used in the control layer of the percutaneous absorption patch of the present invention are not particularly limited as long as a percutaneous absorption patch can be formulated. Examples thereof include petroleum resin (aliphatic hydrocarbon resin, alicyclic hydrocarbon resin, aromatic hydrocarbon resin and the like), rosin resin (rosin, rosin ester and the like), terpene based resin, phenol resin, xylene resin and coumarone indene resin and the like, and medically or pharmaceutically acceptable tackifier resin. One kind may be used singly, or two or more kinds may be used in combination. Preferably, alicyclic hydrocarbon resin, rosin ester and terpene based resin are used.

Examples of the alicyclic hydrocarbon resin include Quintone 1325, Quintone 1340, Quintone 1500, Quintone 1525 L and Quintone 1920 (all manufactured by Zeon Corporation), Arkon P-90, Arkon P-100, Arkon P-115, Arkon P-125, Arkon P-140, Arkon M-90, Arkon M-100, Arkon M-115 and Arkon M135 (all manufactured by Arakawa Chemical Industries, Ltd.), Escorez 5300, Escorez 5320, Escorez 5380 and Escorez 5400 (all manufactured by Exxon Mobil Corporation) and the like. One kind may be used singly, or two or more kinds may be used in combination.

Examples of the rosin ester include glycerol ester of rosin, glycerol ester of hydrogenated rosin, pentaerythritol ester of rosin and the like. Further specifically, Pensel A, Pensel AZ, Pensel C, Pensel D-125, Pensel D-135, Pensel D-160, Pensel KK, Ester Gum AA-G, Ester Gum AA-L, Ester Gum A, Ester Gum AAV, Ester Gum 105, Ester Gum AT, Ester Gum H, Ester Gum HP, Super Ester L, Super Ester A-18, Super Ester A-75, Super Ester A-100, Super Ester A-115, Super Ester A-125, Pinecrystal KE-100, Pinecrystal KE-311 and Pinecrystal KE-359 (all manufactured by Arakawa Chemical Industries, Ltd.), Hariester TF, Haritack ER95, Haritack F85 and Haritack PCJ (all manufactured by Harima Chemicals Group, Inc.) and the like can be mentioned. One kind may be used singly, or two or more kinds may be used in combination.

Examples of the terpene based resin include terpene resin, terpene phenol resin, aromatic modified terpene resin, hydrogenated terpene resin, aromatic modified hydrogenated terpene resin, hydrogenated terpene phenol resin and the like. Further specifically, YS resin PX, YS resin PXN, Daimaron, YS Polystar U, YS Polyster T, YS Polyster S, YS Polyster G, YS Polyster N, YS Polyster K, YS Polyster TH, YS Resin TO, YS Resin TR, Clearon P, Clearon M, Clearon K and YS Polystar UH (all manufactured by YASUHARA CHEMICAL CO., LTD.), Tamanol 803 L and Tamanol 901 (all manufactured by Arakawa Chemical. Industries, Ltd.) and the like. One kind may be used singly, or two or more kinds may be used in combination.

In the percutaneous absorption patch of the present invention, the control layer can appropriately contain, besides those mentioned above, various components acceptable for producing pharmaceutical products, namely, drug dissolving agent, absorption promoter, pH adjuster, antioxidant, filler, crosslinking agent, preservative, ultraviolet absorber and the like, as long as the effect of the present invention is not impaired. The kinds and amounts thereof are not particularly limited as long as they can be formulated as a percutaneous absorption patch.

The drug dissolving agent is not particularly limited as long as it shows a dissolving action on a drug and does not exert a remarkable influence on the stability of the drug. Examples thereof include N-methyl-2-pyrrolidone, isopropyl myristate, isopropyl palmitate, diisopropyl adipate, sorbitan monooleate, propylene glycol caprylate, propylene carbonate, oleyl alcohol, lauryl alcohol, benzyl alcohol, triacetine, crotamiton and 1-menthol and the like. One kind may be used singly, or two or more kinds may be used in combination.

The absorption promoter may be any of the compounds conventionally acknowledged to show a percutaneous absorption promoting action on the skin. Examples thereof include organic acid (lactic acid, propionic acid, cinnamic acid, nicotinic acid, phthalic acid, oxalic acid, fumaric acid, maleic acid, succinic acid, tartaric acid, citric acid, salicylic acid and the like), organic acid ester (myristyl lactate, cetyl lactate, lauryl lactate, methyl cinnamate, methyl salicylate, ethylene glycol salicylate, ethyl acetate, propyl acetate, benzyl acetate and the like), fatty acid having a carbon number of 6-32 (caproic acid, enanthic acid, caprylic acid, pelargric acid, capric acid, undecylic acid, lauric acid, tridecylic acid, myristic acid, pentadecylic acid, palmitic acid, heptadecanoic acid, stearic acid, isostearic acid, oleic acid, nonadecanoic acid, arachidonic acid, linoleic acid, linolenic acid, behenic acid, lignoceric acid, cerotic acid, heptacosanoic acid, montanic acid, melissic acid, elaidic acid, brassidic acid and the like), fatty acid ester and polybasic acid ester (isopropyl myristate, diisopropyl adipate, myristyl palmitate, isopropyl palmitate, oleyl oleate, diethyl sebacate, diisopropyl sebacate, stearyl stearate, ethylhexyl stearate, myristyl myristate and the like), glycerol fatty acid esters (glyceryl myristate, self-emulsifying type glyceryl monostearate, glyceryl monocaprylate, glyceryl tri(caprylate/caprate) and the like), propylene glycol ester of fatty acid (propylene glycol dicaprate, propylene glycol caprylate, propylene glycol dicaprylate, self-emulsifying type propylene glycol stearate, propylene glycol monostearate and the like), sorbitan fatty acid ester (sorbitan monopalmitate, sorbitan monostearate, sorbitan trioleate and the like), sucrose fatty acid ester, aliphatic alcohol (heptyl alcohol, octyl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, oleyl alcohol, nonadecyl alcohol, eicosyl alcohol, ceryl alcohol, melissyl alcohol, cetostearyl alcohol and the like), aromatic alcohol (benzyl alcohol and the like), polyhydric alcohol (ethylene glycol, glycerol, polyethylene glycol, propylene glycol, polypropylene glycol, hexanetriol, butylene glycol and the like), animal and vegetable oils (peppermint oil, turpentine oil, eucalyptus oil, orange oil, almond oil, olive oil, camellia oil, persic oil, soybean oil, sesame oil, corn oil, coconut oil, castor oil, safflower oil, sunflower oil, soybean lecithin and the like), terpene based compound (terpineol, cineol, menthol, isomenthol, menthone, piperitone, pulegone, ionone, carvone, limonene, camphor, borneol, geraniol, thymol, nerol and the like), phenylpropanoid compound (eugenol and the like), pyrrolidone (2-pyrrolidone, 1-methyl-2-pyrrolidone, 5-methyl-2-pyrrolidone, 1,5-dimethylpyrrolidone, 1-ethylpyrrolidone, pyrrothiodecane and the like), urea (urea, thiourea and the like), hydrocarbons (squalane, squalene and the like), azacycloalkane (1-dodecylazacycloheptan-2-one (Azone) and a derivative thereof and the like), polysorbate (polysorbate 20, polysorbate 40, polysorbate 60, polysorbate 65, polysorbate 80 and the like), polyoxyethylene hydrogenated castor oil (polyoxyethylene hydrogenated castor oil, polyoxyethylene hydrogenated castor oil 5, polyoxyethylene hydrogenated castor oil 10, polyoxyethylene hydrogenated castor oil 20, polyoxyethylene hydrogenated castor oil 40, polyoxyethylene hydrogenated castor oil 50, polyoxyethylene hydrogenated castor oil 60, polyoxyethylene hydrogenated castor oil 100 and the like), polyoxyethylene alkyl ethers (polyoxyethylene lauryl ether, polyoxyethylene cetyl ether, polyoxyethylene stearyl ether, polyoxyethylene oleyl ether, polyoxyethylene behenyl ether and the like), triacetine, crotamiton, propylene carbonate and the like. One kind may be used singly, or two or more kinds may be used in combination.

Examples of the pH adjuster include acetic acid, formic acid, lactic acid, tartaric acid, oxalic acid, glycolic acid, malic acid, citric acid, succinic acid, fumaric acid, phosphoric acid, hydrochloric acid, nitric acid, sulfuric acid and salts thereof, sodium hydroxide, potassium hydroxide, calcium hydroxide, arginine, methylamine, ethylamine, propylamine, dimethylamine, diethylamine, dipropylamine, trimethylamine, triethylamine, tripropylamine, monomethanolamine, monoethanolamine, monopropanolamine, dimethanolamine, diethanolamine, dipropanolamine, trimethanolamine, triethanolamine, isopropanolamine, diisopropanolamine, triisopropanolamine, aqueous ammonia, guanidine carbonate, sodium hydrogen carbonate, ammonium carbonate and the like. One kind may be used singly, or two or more kinds may be used in combination.

Examples of the antioxidant include tocopherol and these ester derivative, ascorbic acid, sodium thiosulfate, propyl gallate, ascorbyl stearate, nordihydroguaiuretic acid, sodium edetate, sodium bisulfite, dibutylhydroxytoluene, butylhydroxyanisole and the like. One kind may be used singly, or two or more kinds may be used in combination.

Examples of the filler include calcium carbonate, magnesium carbonate, silicic acid, silicate (aluminum silicate, magnesium silicate and the like), bentonite, kaolin, talc, barium sulfate, calcium sulfate, calcium zincate, zinc oxide, titanium oxide and the like. One kind may be used singly, or two or more kinds may be used in combination.

Examples of the crosslinking agent include thermosetting resin (amino resin, phenol resin, epoxy resin, alkyd resin, unsaturated polyester and the like), organic crosslinking agent (organic peroxide and the like), inorganic crosslinking agent (metal, metal compound and the like), isocyanate compound and block isocyanate compound and the like. One kind may be used singly, or two or more kinds may be used in combination.

Examples of the preservative include thymol, isopropylmethylphenol, benzoic acid and a salt thereof, sorbic acid and a salt thereof, methyl paraoxybenzoate, ethyl paraoxybenzoate, propyl paraoxybenzoate, butyl paraoxybenzoate, benzyl alcohol, benzalkonium chloride, benzethonium chloride and the like. One kind may be used singly, or two or more kinds may be used in combination.

Examples of the ultraviolet absorber include p-aminobenzoic acid derivative, anthranilic acid derivative, salicylic acid derivative, coumarin derivative, amino acid derivative, imidazoline derivative, benzophenone derivative, cinnamic acid derivative, pyrimidine derivative, dioxane derivative and the like. One kind may be used singly, or two or more kinds may be used in combination.

The percutaneous absorption patch of the present invention may be provided with a separating material on a skin-contacting surface on the side opposite to the support. As the separating material, a single layer film selected from the group consisting of a resin film (e.g., composed of polyester such as poly(ethylene terephthalate) and the like, polyethylene, polypropylene, ethylene vinyl acetate copolymer, polyvinyl chloride, polyurethane and the like), paper, a metal film, a cloth and the like, or one obtained by laminating two or more kinds selected from the aforementioned group, and the like can be used. These separating materials preferably have a peel-treated (coated with silicone, fluoro resin and the like) surface on the side in contact with the percutaneous absorption patch.

While the production method of the percutaneous absorption patch of the present invention constituted of the abovementioned constituent components is not particularly limited, the patch can be produced by forming a drug layer and a control layer by a conventional method such as solvent method, hot-melt method and the like, and a method to be newly provided in the future.

For example, when a solvent method is used for the production, the constituent components of the drug layer such as a drug, a base component and the like are first dissolved in an organic solvent to give a uniform dissolution product, and the aforementioned dissolution product is applied to a surface of a separating material and dried to form a drug layer. Then, a support is adhered to the aforementioned drug layer. Also, the constituent components of the control layer such as a base component, a plasticizer and/or a tackifier and the like are dissolved in an organic solvent to give a uniform dissolution product, and the aforementioned dissolution product is applied to a surface of a separating material and dried to form a control layer. The separating material is detached from the drug layer formed earlier, and the drug layer and the control layer are adhered to each other, whereby the percutaneous absorption patch of the present invention can be obtained.

In addition, when a hot-melt method is used for the production, the constituent components of the drug layer such as a drug, a base component and the like are first mixed by heating to give a uniform molten product, the aforementioned molten product is applied to a surface of a separating material to form a drug layer and a support is adhered thereto. Also, the constituent components of the control layer such as a base component, a plasticizer and/or a tackifier and the like are mixed by heating to give a uniform molten product, and the aforementioned molten product is applied to a surface of a separating material to form a control layer. The separating material is detached from the drug layer formed earlier, and the drug layer and the control layer are adhered to each other, whereby the percutaneous absorption patch of the present invention can be obtained.

The drug layer and the control layer of the percutaneous absorption patch of the present invention can also be respectively produced by different production methods, and the drug layer can also be formed by applying a dissolved product or molten product on a support surface instead of the separating material.

Also, as long as the effect of the present invention is not impaired, the application method of the dissolved product or molten product is not particularly limited, and a method including forming a drug layer (or control layer) and applying a control layer (or drug layer) thereon, a simultaneous multi-layer coating method, a pattern coating method and the like can be adopted besides the method of respectively applying the drug layer and the control layer described above.

The organic solvent to be used for production by a solvent method is not particularly limited and any can be used as long as it is volatilized in a step of drying by heating after a coating step. For example, lower alcohol, toluene, ethyl acetate, butyl acetate, acetone, dibutyl ether, tetrahydrofuran, xylene, hexane, cyclohexane and the like can be mentioned.

The shape of the percutaneous absorption patch of the present invention is not particularly limited as long as it does not hinder the adhering operation of the percutaneous absorption patch itself, adhesiveness to the skin during adhering and the like. Examples of the flat plane shape of the percutaneous absorption patch itself include a shape outlined by a substantially straight line such as triangle, rectangle, polygon (pentagon and the like) and the like, a shape outlined by a curve such as ellipse, circular shape and the like, a shape outlined by both a substantially straight line and curve and the like.

The skin adhesion area when the percutaneous absorption patch of the present invention is applied to human is not particularly limited as long as it expresses a desired efficacy and can be adhered to the human skin. However, when the skin adhesion area is too small, a desired efficacy cannot be obtained or the drug absorption amount per unit area needs to be set markedly high, which is unpreferable since it places an excessive burden on the skin. An excessively large skin adhesion area is unpreferable because QOL of the patients is impaired during use of the patch due to deteriorated followability to the skin, an uncomfortable feeling and the like. Therefore, the skin adhesion area of the percutaneous absorption patch of the present invention is preferably 1-100 $cm^2$, more preferably 2-80 $cm^2$, most preferably 4-50 $cm^2$.

In the percutaneous absorption patch of the present invention, the thickness of the drug layer is preferably 10-400 µm, more preferably 30-200 µm. When the thickness of the drug layer is thinner than 10 µm, uniform coating sometimes becomes difficult, and when it is thicker than 400 µm, the drug layer may extrude or the followability to the skin may decrease during preservation and adhesion.

In the percutaneous absorption patch of the present invention, the thickness of the control layer is preferably 10-200 µm, more preferably 15-100 µm. When the thickness of the control layer is thinner than 10 µm, uniform coating sometimes becomes difficult, and when it is thicker than 200 µm, the skin permeation amount of the drug may decrease.

EXAMPLES

While the present invention is explained in more detail in the following by Examples, the present invention is not limited thereby.

As the components contained in the drug layer and the control layer shown in the following Table 1, respective starting materials shown below were used.

(1) nalfurafine: produced according to a known production method (e.g., production methods described in JP-B-2525552 and the like) and used.

(2) styrene-isoprene-styrene block copolymer: "JSRSIS5505P" (manufactured by JSR Corporation) (3) polyisobutylene: "Oppanol B-200" (manufactured by BASF Japan Ltd.)

(4) rosin ester: "Pinecrystal KE-311" (manufactured by Arakawa Chemical Industries, Ltd.)

(5) terpene based resin: "YS Resin PX1150N" (manufactured by YASUHARA CHEMICAL CO., LTD.)

(6) alicyclic hydrocarbon resin: "Arkon P-125" (manufactured by Arakawa Chemical Industries, Ltd.)

(7) liquid paraffin: "KAYDOL" (manufactured by SONNEBORN LLC.)

Example 1

Percutaneous Absorption Patch 1

Based on the formulation shown in Table 1, the below-mentioned Preparation Method 1 was performed to prepare the percutaneous absorption patch 1 of the present invention. Using the obtained percutaneous absorption patch 1, a rat skin permeation test was performed according to Experimental Example 1. As a result, the maximum value of the drug skin permeation amount per unit time was 290.2 $ng/cm^2/hr$, and an excess amount of the drug did not permeate through the skin in a short time even when applied to a skin after detachment of the horny cell layer. In addition, drug skin permeation amount per unit time 10 hr later was 264.6 $ng/cm^2/hr$, and a ratio of the drug skin permeation amount per unit time 10 hr later to the maximum value of the drug skin permeation amount per unit time (drug skin permeation amount per unit time 10 hr later/maximum value of drug skin permeation amount per unit time) was 0.91, thereby showing that a given drug skin permeation amount can be maintained. The results are shown in Table 2.

TABLE 1

| | component | Example 1 | Example 2 | Example 3 | Example 4 | Example 5 | Example 6 | Example 7 | Comparative Example 1 |
|---|---|---|---|---|---|---|---|---|---|
| drug layer | nalfurafine | 0.1 | 0.1 | 0.1 | 0.1 | 0.1 | 0.1 | 0.1 | 0.1 |
| | styrene-isoprene-styrene block copolymer | 40 | 40 | 40 | 40 | 40 | 40 | 40 | 40 |
| | liquid paraffin | rest | rest | rest | rest | rest | rest | rest | rest |
| | total | 100 | 100 | 100 | 100 | 100 | 100 | 100 | 100 |
| control layer | polyisobutylene | 60 | 60 | 60 | 60 | 60 | 40 | 40 | — |
| | rosin ester | 40 | — | — | — | 20 | 20 | 40 | — |
| | terpene based resin | — | 40 | — | — | — | — | — | — |
| | alicyclic hydrocarbon resin | — | — | 40 | — | — | — | — | — |
| | liquid paraffin | — | — | — | 40 | 20 | 40 | 20 | — |
| | total | 100 | 100 | 100 | 100 | 100 | 100 | 100 | — |

Numerical values in the Table show contents (mass %) of respective components contained in drug layer and control layer.

(Preparation Method 1)

Nalfurafine was dissolved in toluene, a styrene-isoprene-styrene block copolymer was added and the mixture was dissolved. Liquid paraffin was added and mixed to give a drug-containing coating solution. The obtained drug-containing coating solution was applied to and spread on a separating material, and toluene was removed by drying to give a drug layer having a given plaster thickness (100 μm), and the drug layer was adhered to a support.

Separately, polyisobutylene dissolved in hexane and rosin ester dissolved in toluene were mixed to give a coating solution, the coating solution was applied to and spread on a separating material, and hexane and toluene were removed by drying to give a control layer having a given plaster thickness (20 μm). The separating material was peeled off from the aforementioned drug layer and the drug layer was adhered to the aforementioned control layer to give percutaneous absorption patch 1.

Experimental Example 1

Rat Skin Permeation Test

Using the percutaneous absorption patch 1 of the aforementioned Example 1 and percutaneous absorption patches 2-7 of the below-mentioned Examples 2-7, and comparison patch 1 of Comparative Example 1, rat skin permeation tests were performed by the method shown below.

Abdominal skin of HWY hairless rat (male, 8-week-old, body weight about 250 g, purchased from Japan SLC, Inc.) was isolated after detaching the horny cell layer with a surgical tape and used as a test skin. The obtained test skin was mounted on a 2-chamber diffusion cell such that the corium side was the receiver side, and respective patches of the Examples and Comparative Example were punched into a circle with diameter 1 cm and applied to the side from which the horny cell layer was detached. The receiver side of the 2-chamber diffusion cell was filled with phosphate buffered saline (pH=7.4) (hereinafter to be referred to as "receiver solution") and the stirring was continued until completion of the test. The jacket temperature of the 2-chamber diffusion cell was kept at about 38° C., the receiver solution was sampled at 0.5, 1, 1.5, 2, 2.5, 3, 4, 6, 8 and 10 hr after application of each patch, and an equal amount of a fresh receiver solution was supplemented. The amount of the drug in the sampled receiver solution was measured by high performance liquid chromatography, from which the cumulative drug skin permeation amount of nalfurafine that permeated the skin was determined, and a drug skin permeation amount per unit time (ng/cm$^2$/hr) of nalfurafine was calculated. The drug skin permeation amount per unit time was calculated by dividing a difference between a cumulative permeation amount per unit area at each sampling time and a cumulative permeation amount per unit area at the previous sampling time by a sampling interval (hr). The calculated maximum value of the drug skin permeation amount per unit time, the calculated drug skin permeation amount per unit time 10 hr later and a ratio of the drug skin permeation amount per unit time 10 hr later to the maximum value of the drug skin permeation amount per unit time (drug skin permeation amount per unit time 10 hr later/maximum value of drug skin permeation amount per unit time) are shown in Table 2.

TABLE 2

| | drug skin permeation amount per unit time (ng/cm$^2$/hr) | | drug skin permeation amount per unit time 10 hr later/maximum value of drug skin permeation amount per unit time |
|---|---|---|---|
| | maximum value | 10 hr later | |
| Example 1 | 290.2 | 264.6 | 0.91 |
| Example 2 | 210.6 | 169.4 | 0.80 |
| Example 3 | 250.7 | 201.8 | 0.80 |
| Example 4 | 389.0 | 246.0 | 0.63 |
| Example 5 | 334.4 | 295.7 | 0.88 |
| Example 6 | 453.6 | 357.0 | 0.79 |
| Example 7 | 372.7 | 307.3 | 0.82 |
| Comparative Example 1 | 1624.0 | 159.7 | 0.10 |

Example 2

Percutaneous Absorption Patch 2

Percutaneous absorption patch 2 was obtained by Preparation Method 1 as in Example 1 except that terpene based resin was used instead of rosin ester. Using the obtained percutaneous absorption patch 2, a rat skin permeation test was performed according to Experimental Example 1. The results are shown in Table 2.

As shown in Table 2, the maximum value of the drug skin permeation amount per unit time was 210.6 ng/cm$^2$/hr, and an excess amount of the drug did not permeate through the skin in a short time. In addition, drug skin permeation amount per unit time 10 hr later was 169.4 ng/cm$^2$/hr, and a ratio of the drug skin permeation amount per unit time 10 hr later to the maximum value of the drug skin permeation amount per unit time (drug skin permeation amount per unit time 10 hr later/maximum value of drug skin permeation amount per unit time) was 0.80, thereby showing that a given drug skin permeation amount can be maintained.

Example 3

Percutaneous Absorption Patch 3

Percutaneous absorption patch 3 was obtained by Preparation Method 1 as in Example 1 except that alicyclic hydrocarbon resin was used instead of rosin ester. Using the obtained percutaneous absorption patch 3, a rat skin permeation test was performed according to Experimental Example 1. The results are shown in Table 2.

As shown in Table 2, the maximum value of the drug skin permeation amount per unit time was 250.7 ng/cm$^2$/hr, and an excess amount of the drug did not permeate through the skin in a short time. In addition, drug skin permeation amount per unit time 10 hr later was 201.8 ng/cm$^2$/hr, and a ratio of the drug skin permeation amount per unit time 10 hr later to the maximum value of the drug skin permeation amount per unit time (drug skin permeation amount per unit time 10 hr later/maximum value of drug skin permeation amount per unit time) was 0.80, thereby showing that a given drug skin permeation amount can be maintained.

Example 4

Percutaneous Absorption Patch 4

Percutaneous absorption patch 4 was obtained by Preparation Method 1 as in Example 1 except that liquid paraffin was used instead of rosin ester. Using the obtained percutaneous absorption patch 4, a rat skin permeation test was performed according to Experimental Example 1. The results are shown in Table 2.

As shown in Table 2, the maximum value of the drug skin permeation amount per unit time was 389.0 ng/cm$^2$/hr, and an excess amount of the drug did not permeate through the skin in a short time. In addition, drug skin permeation amount per unit time 10 hr later was 246.0 ng/cm$^2$/hr, and a ratio of the drug skin permeation amount per unit time 10 hr later to the maximum value of the drug skin permeation amount per unit time (drug skin permeation amount per unit time 10 hr later/maximum value of drug skin permeation amount per unit time) was 0.63, thereby showing that a given drug skin permeation amount can be maintained.

Example 5

Percutaneous Absorption Patch 5

Percutaneous absorption patch 5 was obtained by Preparation Method 1 as in Example 1 except that the blended amount of rosin ester was changed from 40 mass % to 20 mass %, and 20 mass % of liquid paraffin was blended.

Using the obtained percutaneous absorption patch 5, a rat skin permeation test was performed according to Experimental Example 1. The results are shown in Table 2.

As shown in Table 2, the maximum value of the drug skin permeation amount per unit time was 334.4 ng/cm$^2$/hr, and an excess amount of the drug did not permeate through the skin in a short time. In addition, drug skin permeation amount per unit time 10 hr later was 295.7 ng/cm$^2$/hr, and a ratio of the drug skin permeation amount per unit time 10 hr later to the maximum value of the drug skin permeation amount per unit time (drug skin permeation amount per unit time 10 hr later/maximum value of drug skin permeation amount per unit time) was 0.88, thereby showing that a given drug skin permeation amount can be maintained.

Example 6

Percutaneous Absorption Patch 6

Percutaneous absorption patch 6 was obtained by Preparation Method 1 as in Example 5 except that the blended amount of polyisobutylene was changed from 60 mass % to 40 mass %, and the blended amount of liquid paraffin was changed from 20 mass % to 40 mass %. Using the obtained percutaneous absorption patch 6, a rat skin permeation test was performed according to Experimental Example 1. The results are shown in Table 2.

As shown in Table 2, the maximum value of the drug skin permeation amount per unit time was 453.6 ng/cm$^2$/hr, and an excess amount of the drug did not permeate through the skin in a short time. In addition, drug skin permeation amount per unit time 10 hr later was 357.0 ng/cm$^2$/hr, and a ratio of the drug skin permeation amount per unit time 10 hr later to the maximum value of the drug skin permeation amount per unit time (drug skin permeation amount per unit time 10 hr later/maximum value of drug skin permeation amount per unit time) was 0.79, thereby showing that a given drug skin permeation amount can be maintained.

Example 7

Percutaneous Absorption Patch 7

Percutaneous absorption patch 7 was obtained by Preparation Method 1 as in Example 5 except that the blended amount of polyisobutylene was changed from 60 mass % to 40 mass %, and the blended amount of rosin ester was changed from 20 mass % to 40 mass %. Using the obtained percutaneous absorption patch 7, a rat skin permeation test was performed according to Experimental Example 1. The results are shown in Table 2.

As shown in Table 2, the maximum value of the drug skin permeation amount per unit time was 372.7 ng/cm$^2$/hr, and an excess amount of the drug did not permeate through the skin in a short time. In addition, drug skin permeation amount per unit time 10 hr later was 307.3 ng/cm$^2$/hr, and a ratio of the drug skin permeation amount per unit time 10 hr later to the maximum value of the drug skin permeation amount per unit time (drug skin permeation amount per unit time 10 hr later/maximum value of drug skin permeation amount per unit time) was 0.82, thereby showing that a given drug skin permeation amount can be maintained.

Comparative Example 1

Comparison Patch 1

Comparison patch 1 was obtained by Preparation Method 1 as in Example 1 except that a control layer was not adhered to a drug layer. Using the obtained comparison patch 1, a rat skin permeation test was performed according to Experimental Example 1. The results are shown in Table 2.

As shown in Table 2, the maximum value of the drug skin permeation amount per unit time was 1624.0 ng/cm$^2$/hr, which shows that an excess amount of the drug permeated through the skin in a short time when applied to a skin after detachment of the horny cell layer. In addition, drug skin permeation amount per unit time 10 hr later was 159.7 ng/cm$^2$/hr, and a ratio of the drug skin permeation amount per unit time 10 hr later to the maximum value of the drug skin permeation amount per unit time (drug skin permeation amount per unit time 10 hr later/maximum value of drug skin permeation amount per unit time) was 0.10, and a given drug skin permeation amount could not be maintained after 10 hr.

INDUSTRIAL APPLICABILITY

The present invention relates to a nalfurafine-containing percutaneous absorption patch capable of maintaining a given level of drug skin permeation amount without permeation of an excess amount of the drug through the skin in a short time even when applied to the skin in which the horny cell layer and the like are damaged and the skin barrier function is insufficient, by laminating a control layer on a drug layer containing nalfurafine, and can be utilized industrially sufficiently.

This application is based on a patent application No. 2015-126282 filed in Japan, the contents of which are incorporated in full herein.

The invention claimed is:

1. A percutaneous absorption patch comprising a support, a drug layer and a control layer which are laminated successively, wherein said drug layer comprises 0.0001-10 mass % of at least one drug selected from the group consisting of nalfurafine and a salt thereof, and a styrene block copolymer as a base, and said control layer comprises a chain hydrocarbon polymer and 10-90 mass % of at least one substance selected from the group consisting of a plasticizer and a tackifier.

2. The percutaneous absorption patch according to claim 1, wherein the styrene block copolymer is a styrene-isoprene-styrene block copolymer.

3. The percutaneous absorption patch according to claim 1, wherein said control layer comprises polyisobutylene as the chain hydrocarbon polymer.

4. The percutaneous absorption patch according to claim 1, wherein said plasticizer is liquid paraffin.

5. The percutaneous absorption patch according to claim 1, wherein said tackifier is at least one kind selected from the group consisting of rosin ester, a terpene-based resin and an alicyclic hydrocarbon resin.

6. The percutaneous absorption patch according to claim 1, wherein, in a rat skin permeation test, the maximum value of a drug skin permeation amount per unit time is not more than 1000 ng/cm$^2$/hr.

7. The percutaneous absorption patch according to claim 1, wherein, in a rat skin permeation test, a ratio of the drug skin permeation amount per unit time 10 hr later to the maximum value of the drug skin permeation amount per unit time (drug skin permeation amount per unit time 10 hr later/maximum value of drug skin permeation amount per unit time) is not less than 0.5.

8. The percutaneous absorption patch according to claim 2, wherein, in a rat skin permeation test, the maximum value of a drug skin permeation amount per unit time is not more than 1000 ng/cm$^2$/hr.

9. The percutaneous absorption patch according to claim 2, wherein, in a rat skin permeation test, a ratio of the drug skin permeation amount per unit time 10 hr later to the maximum value of the drug skin permeation amount per unit time (drug skin permeation amount per unit time 10 hr later/maximum value of drug skin permeation amount per unit time) is not less than 0.5.

* * * * *